(12) United States Patent
Unai et al.

(10) Patent No.: US 10,813,535 B2
(45) Date of Patent: Oct. 27, 2020

(54) MEDICAL SYSTEM AND MEDICAL DEVICE HOLDING APPARATUS

(71) Applicant: OLYMPUS CORPORATION, Tokyo (JP)

(72) Inventors: Ryutaro Unai, Tokyo (JP); Kazuo Banju, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/727,106

(22) Filed: Dec. 26, 2019

(65) Prior Publication Data

US 2020/0129052 A1    Apr. 30, 2020

Related U.S. Application Data

(63) Continuation of application No. PCT/JP2017/024187, filed on Jun. 30, 2017.

(51) Int. Cl.
| | |
|---|---|
| *F16M 11/04* | (2006.01) |
| *A61B 1/00* | (2006.01) |
| *A61B 90/50* | (2016.01) |
| *A61B 1/313* | (2006.01) |

(52) U.S. Cl.
CPC .......... *A61B 1/00149* (2013.01); *A61B 90/50* (2016.02); *A61B 1/3132* (2013.01); *A61B 2090/504* (2016.02)

(58) Field of Classification Search
CPC .......... A61B 2090/504; A61B 1/00149; G02B 7/001; F16M 2200/047; B25J 19/002
See application file for complete search history.

(56) References Cited

U.S. PATENT DOCUMENTS

| | | | | | |
|---|---|---|---|---|---|
| 4,668,057 A | * | 5/1987 | Kleinberg | ............ | F16M 11/046 359/384 |
| 5,173,803 A | * | 12/1992 | Heller | .................. | F16M 11/126 359/384 |

(Continued)

FOREIGN PATENT DOCUMENTS

| | | |
|---|---|---|
| EP | 3127468 A1 | 2/2017 |
| JP | 2006-061272 A | 3/2006 |

(Continued)

OTHER PUBLICATIONS

Sep. 19, 2017 International Search Report issued in International Patent Application No. PCT/JP2017/024187.

*Primary Examiner* — Bradley Duckworth
(74) *Attorney, Agent, or Firm* — Oliff PLC (57) ABSTRACT

A medical device holding apparatus includes a first medical device; a second medical device having a different weight from the first medical device; a base having a counterweight; an arm having a first end coupled to the counterweight via a link mechanism; an adapter for attaching the first medical device or the second medical device to a second end of the arm; a first balance correction member attached to the adapter to attain a weight balance between both sides of the arm in a case where the first medical device is attached to the adapter; and a second balance correction member attached to the adapter to attain a weight balance between the first end and the second end of the arm in a case where the second medical device is attached to the adapter.

12 Claims, 8 Drawing Sheets

(56) References Cited

U.S. PATENT DOCUMENTS

| | | | | |
|---|---|---|---|---|
| 5,441,505 A * | 8/1995 | Nakamura | F16M 11/08 | 414/917 |
| 5,480,114 A * | 1/1996 | Nakamura | F16M 11/126 | 248/123.2 |
| 5,812,301 A * | 9/1998 | Nakamura | A61B 90/25 | 359/384 |
| 5,825,536 A * | 10/1998 | Yasunaga | A61B 90/25 | 359/384 |
| 6,045,104 A * | 4/2000 | Nakamura | F16M 11/10 | 248/123.11 |
| 6,963,444 B2 * | 11/2005 | Brenner | F16M 11/10 | 248/123.2 |
| 7,189,246 B2 * | 3/2007 | Otsuka | A61B 90/50 | 600/102 |
| 7,846,086 B2 * | 12/2010 | Brenner | G02B 7/001 | 174/77 R |
| 8,205,847 B2 * | 6/2012 | Dorris | F16M 11/041 | 248/222.52 |
| 8,342,467 B2 * | 1/2013 | Stachowski | A61B 8/00 | 248/280.11 |
| 8,718,898 B2 * | 5/2014 | Schaible | F16M 11/20 | 180/11 |
| 8,979,042 B2 * | 3/2015 | Doi | F16M 11/2021 | 248/123.11 |
| 9,400,079 B2 * | 7/2016 | Doi | F16M 11/18 | |
| 2013/0206934 A1 * | 8/2013 | Schutz | G02B 7/001 | 248/123.2 |
| 2016/0252699 A1 | 9/2016 | Yi et al. | | |
| 2019/0209264 A1 * | 7/2019 | Seo | A61B 90/50 | |
| 2019/0377149 A1 * | 12/2019 | Ishima | G02B 7/001 | |

FOREIGN PATENT DOCUMENTS

| | | |
|---|---|---|
| JP | 2006-254974 A | 9/2006 |
| JP | 2014-113237 A | 6/2014 |
| JP | 2016-522044 A | 7/2016 |
| WO | 2016/157571 A1 | 10/2016 |

* cited by examiner

MEDICAL SYSTEM AND MEDICAL DEVICE HOLDING APPARATUS

CROSS REFERENCE TO RELATED APPLICATION

This application is a continuation application based on PCT Patent Application No. PCT/JP2017/024187, filed Jun. 30, 2017, the content of which is incorporated herein by reference.

TECHNICAL FIELD

The disclosed embodiments relate to a medical device holding apparatus and a medical system.

BACKGROUND

Holding apparatuses for holding medical devices have been used in laparoscopic surgery conducted using an endoscope and the like, for the purpose of preventing the hands of users who are holding a medical device such as an endoscope or a surgical instrument from shaking, reducing their fatigue, and the like.

A holding apparatus can have a support column, a movable arm connected to the support column, and a balance adjusting mechanism that attains counterbalancing for the entire holding apparatus with a medical instrument attached to the movable arm. However, the balancing adjustment mechanism requires the user to perform adjustment operations in an unclean area during surgery.

SUMMARY

The present disclosure is directed to a medical device holding apparatus including a first medical device; a second medical device having a different weight from the first medical device; a base having a counterweight; an arm having a first end coupled to the counterweight via a link mechanism; an adapter for attaching the first medical device or the second medical device to a second end of the arm; a first balance correction member attached to the adapter to attain a weight balance between both sides of the arm in a case where the first medical device is attached to the adapter; and a second balance correction member attached to the adapter to attain a weight balance between the first end and the second end of the arm in a case where the second medical device is attached to the adapter.

When a weight of a combination of the adapter, the first medical device, and the first balance correction member is assumed to be M1 and a weight of a combination of the adapter, the second medical device and the second balance correction member is assumed to be M2, the following relationship is satisfied $1.15 \geq M2/M1 \geq 0.85$.

According to an exemplary embodiment of the present disclosure, a medical device holding apparatus includes a base having a counterweight; an arm having a first end coupled to the counterweight via a link mechanism; a medical device attached to a second end of the arm via an adapter; and a balance correction member attached to the adapter to attain a weight balance between the first end and the second end of the arm in a state in which the medical device is attached to the arm. The balance correction member is replaceable according to a type of the medical device to be attached to the arm.

A plurality of types of the balance correction member may be provided and a balance correction member is configured to be selected according to a weight of the medical device to be attached to the arm.

The medical device holding apparatus may include a drape configured to be attached between the arm and the adapter.

According to an exemplary embodiment of the present disclosure, a medical device holding apparatus includes a base having a counterweight; an arm that is movable with respect to the base and has a first end coupled to the counterweight via a link mechanism; a medical device attached to a second end of the arm via an adapter; and a balance correction member that is configured to adjust a weight balance between the first end and the second end of the arm so that the arm is held at a desired position in a state in which the medical device is attached to the arm via the adapter.

DETAILED DESCRIPTION OF THE PREFERRED EMBODIMENTS

Embodiments of the present invention will be described below with reference to the drawings.

Figure 1:
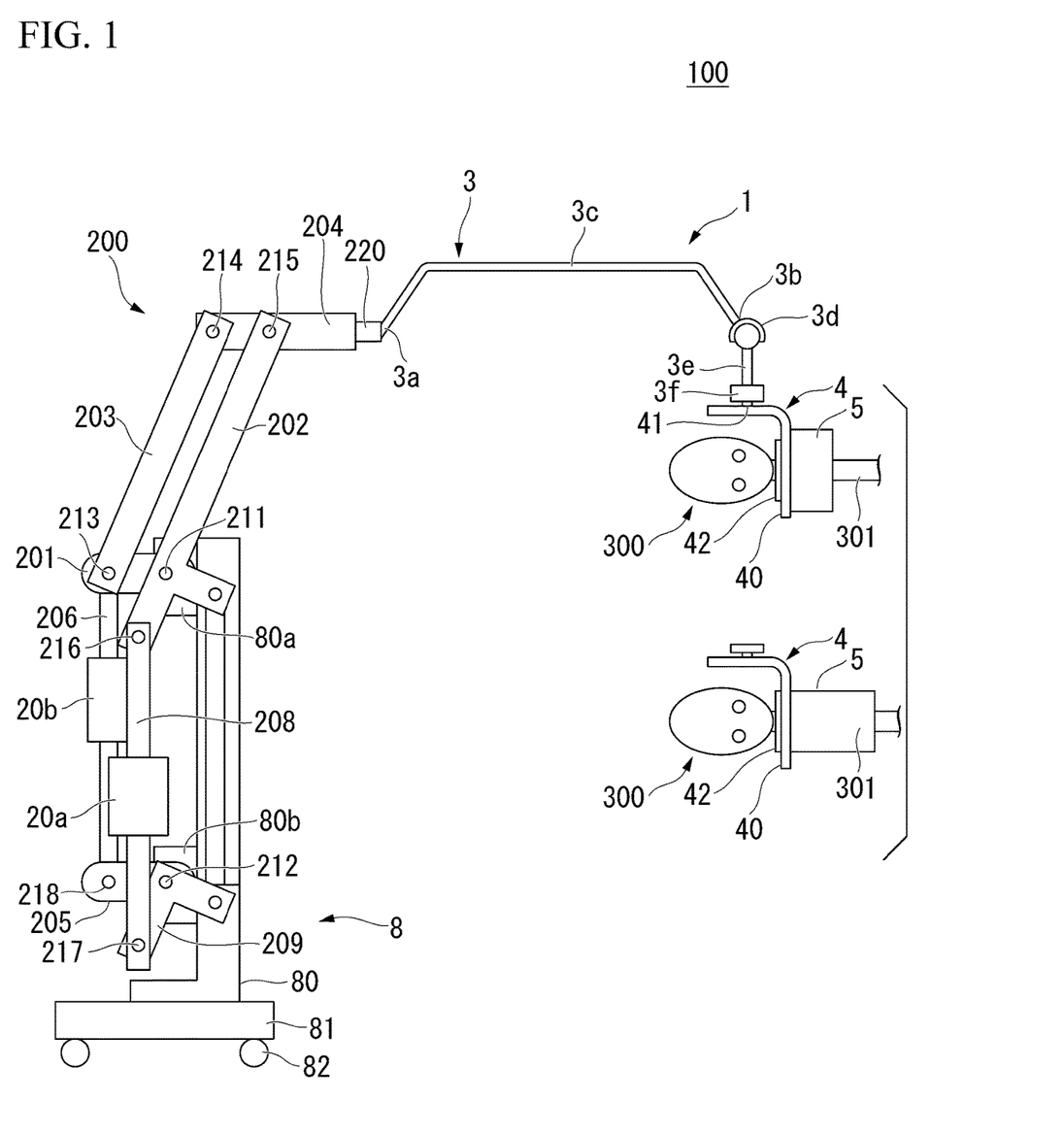
FIG. 1 is an overall view of a medical device holding apparatus and a medical system according to the disclosed embodiments.
Figure 2:
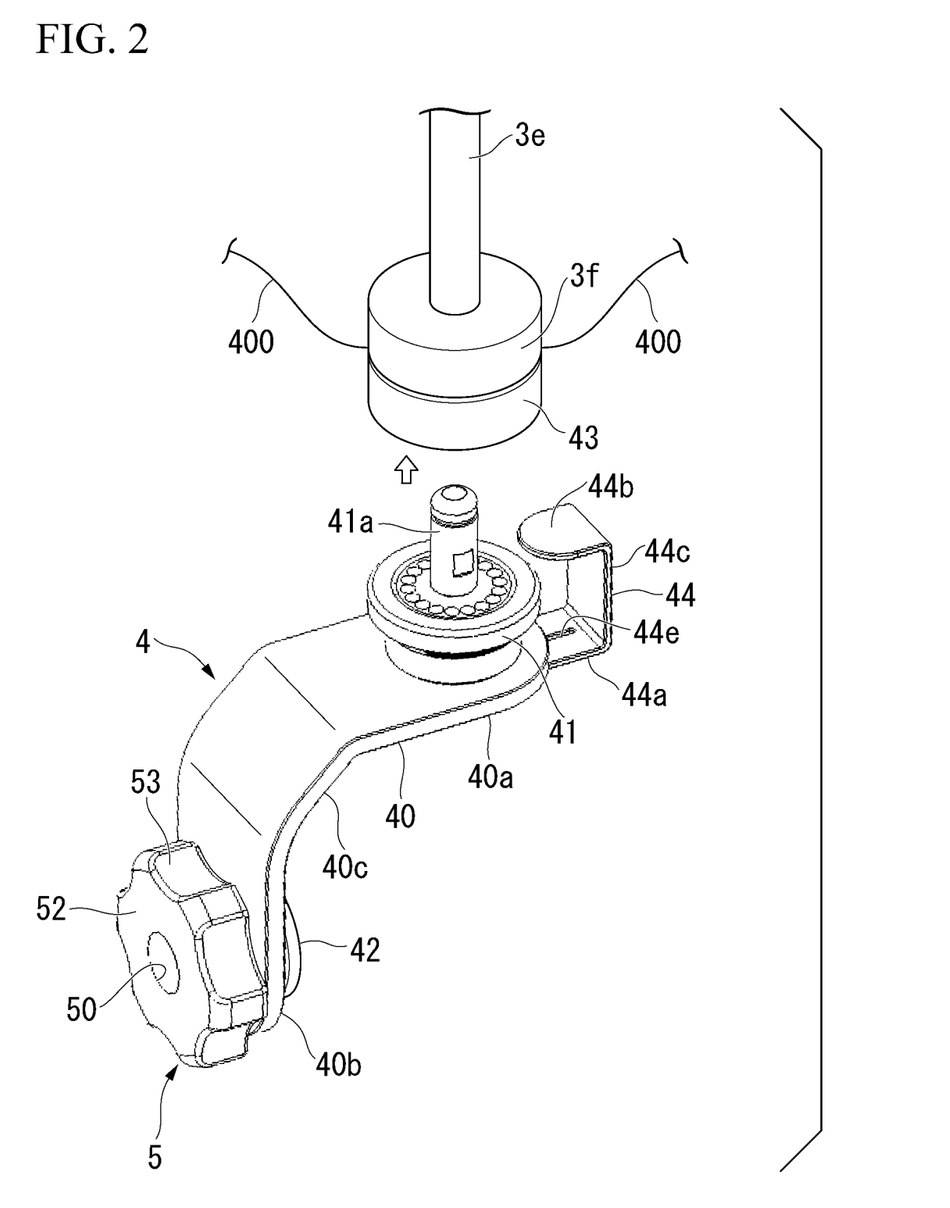
FIG. 2 is a perspective view showing an adapter and a balance correction member of the medical device holding apparatus shown in FIG. 1.
Figure 3:
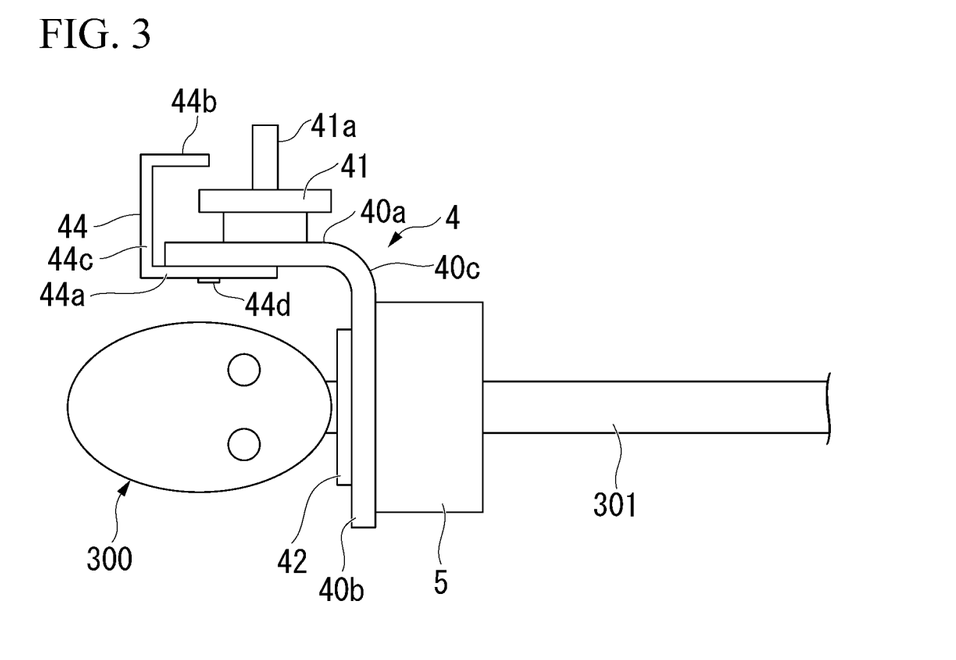
FIG. 3 is a side view showing a state in which a medical device is attached to the adapter shown in FIG. 1.
Figure 4:
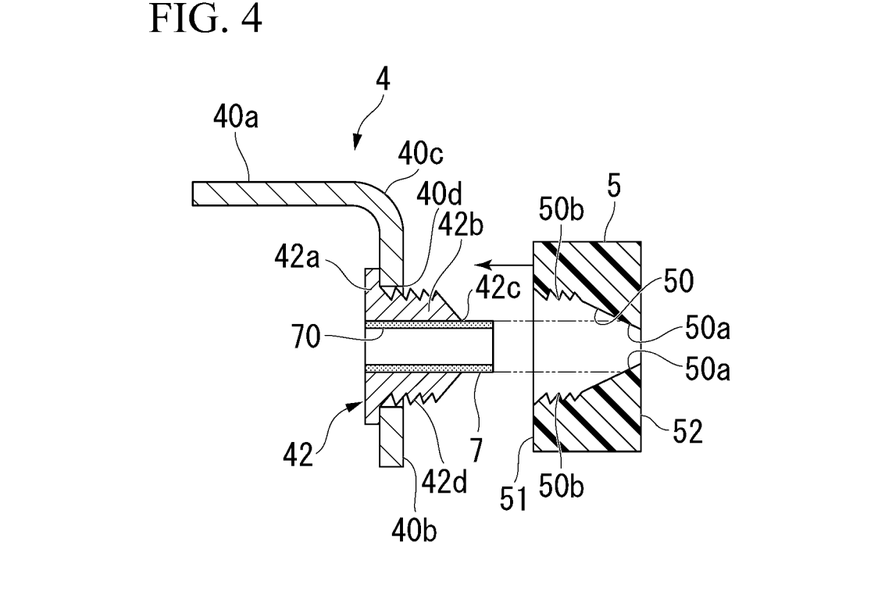
FIG. 4 is a cross-sectional view showing the adapter and the balance correction member of the medical device holding apparatus shown in FIG. 1.

A medical device holding apparatus 1 and a medical system 100 according to the disclosed embodiments will be described. FIG. 1 is an overall view of the medical device holding apparatus 1 according to the disclosed embodiments. FIG. 2 is a perspective view showing an adapter 4 (connection assembly) and a balance correction member 5 (weight) of the medical device holding apparatus 1. FIG. 3 is a side view showing a state in which a medical device 300 is attached to the adapter 4. FIG. 4 is a cross-sectional view showing the adapter and the balance correction member 5. In FIG. 4, an arm connection part 41 and a slide lock 44 are not shown.

The medical system 100 has the medical device holding apparatus 1, a plurality of medical devices 300, and a plurality of balance correction members 5 (a first weight and a second weight) as shown in FIG. 1. For the medical devices 300, devices of different types having different sizes, for example, endoscopes, various treatment tools, and the like, are used. Each of the medical devices 300 has a long part 301. The medical device holding apparatus 1 has a base 8, an arm 3, the adapters 4, and the balance correction members 5.

The base 8 has a supporter 81, a support column 80, an arm moving mechanism 200, and counterweights 20a, and 20b.

The supporter 81 is a base that is placed directly or indirectly on a floor. In the medical device holding apparatus 1 shown in FIG. 1, the supporter 81 is directly placed on a floor. The supporter 81 includes casters 82 with a known stopper function. The supporter 81 enables the medical device holding apparatus 1 to easily move on the floor and to be stopped to prevent the medical device holding apparatus 1 from moving on the floor.

Instead of the configuration in which the supporter 81 is placed on a floor, the supporter 81 may be configured to include a coupling part that couples the supporter to, for example, an operating table, a surgery assisting device, and the like and to fix the supporter to the operating table, the surgery assisting device, and the like.

The support column 80 is a member having a lower end part attached to the supporter 81 on the floor and stands in the vertical direction. The support column 80 is attached to the supporter 81 such that the support column 80 can horizontally rotate around the axis of the support column 80 with respect to the supporter 81. An upper link supporter 80a and a lower link supporter 80b are provided respectively on an upper part and a lower part of the support column 80. The upper link supporter 80a and a lower link supporter 80b project from the support column in the horizontal direction.

The arm moving mechanism 200 is a parallel link mechanism attached to the support column 80. The arm moving mechanism 200 is axially supported by the upper link supporter 80a and the lower link supporter 80b via a first pivot shaft 211 and a second pivot shaft 212. The arm moving mechanism 200 has an arm coupling part 220 at an end thereof positioned at an upper end of the support column 80. A proximal end part 3a of the arm 3 is attached to the arm coupling part 220.

The arm moving mechanism 200 has a first parallel link mechanism, a second parallel link mechanism, and a third parallel link mechanism. The first parallel link mechanism is provided between the upper link supporter 80a and the arm coupling part 220. The second parallel link mechanism and the third parallel link mechanism are provided between the upper link supporter 80a and the lower link supporter 80b.

The first parallel link mechanism has four links 201, 202, 203, and 204 that are pivotably coupled to one another via pivot shafts 211, 213, 214, and 215. In the first parallel link mechanism, the link 201, and the link 202 which are disposed at a lower part thereof are connected to each other via the upper link supporter 80a and the first pivot shaft 211.

The second parallel link mechanism has a plurality of links 202, 208, and 209. The links 202, 208, and 209 are coupled to one another via pivot shafts 217 and 216 and connected to the upper link supporter 80a and the lower link supporter 80b. The first counterweight 20a is attached to one link 208 of the second parallel link mechanism. The link 208 extends in the vertical direction. The second parallel link mechanism has a function of maintaining a state in which the first counterweight 20a hangs in the vertical direction at all times.

The third parallel link mechanism has a plurality of links 201, 205, and 206 that are coupled to one another via pivot shafts 211 and 213 and are connected to the upper link supporter 80a and the lower link supporter 80b. The second counterweight 20b is attached to one link 206 of the third parallel link mechanism, the link extending in the vertical direction. The third parallel link mechanism has a function of maintaining a state in which the second counterweight 20b hangs in the vertical direction at all times.

The arm moving mechanism 200 is not limited to a parallel link mechanism of the present embodiment, and any one can be applied to as long as it has a configuration of supporting an arm in a movable state with respect to a support such as a support column, and another known mechanism. For example, a movable mechanism composed of a pulley and a wire, a movable mechanism using a motor and a detector, or the like may be used as the arm moving mechanism. In addition, the number of counterweights is not limited to two.

The proximal end part 3a of the arm 3 is connected to the arm coupling part 220 (base). The arm 3 is movably attached with respect to the base 8. A swing arm 3e is provided at a distal end part 3b of the arm 3. An end part of the swing arm 3e has a spherical shape and is engaged with a grip part 3d having a circular shape at the distal end part 3b of the arm 3. The swing arm 3e is engaged with the grip part 3d such that the swing arm can swing around an end part of the spherical shape.

Further, the swing arm 3e is not limited to the above-described configuration as long as the swing arm is engaged with the grip part 3d so as to swing.

A device coupling part 3f for attaching the medical device 300 is provided at the lower end of the swing arm 3e. The arm 3 has a horizontal part 3c between the proximal end part 3a and the distal end part 3b extending in the horizontal direction. The arm 3 is configured to change a height of the horizontal part 3c by using the arm moving mechanism 200.

The adapter 4 is configured to be detachably attached to the device coupling part 3f at the distal end part 3b of the arm 3. In addition, the adapter 4 is a member configured to allow the medical device 300 to be detachably attached.

The adapter 4 has an adapter body 40, an arm connection part 41, a medical device holding part 42, and a slide lock 44 as shown in FIGS. 2 and 3. The adapter body 40 is a plate-like member having a curved shape and is composed of a first flat surface 40a, a second flat surface 40b, and a curved part 40c.

The arm connection part 41 is provided on the first flat surface 40a. The arm connection part 41 has a shaft 41a and is configured such that the shaft 41a is inserted and fitted into the device coupling part 3f.

The slide lock 44 is a substantially U-shaped member. The slide lock 44 is formed such that a contact part 44a and a locking part 44b that are two flat surfaces extending parallel to each other are connected via a vertical flat surface 44c as shown in FIGS. 2 and 3. A slit 44e is formed in the contact part 44a. The contact part 44a comes in contact with a back surface of the first flat surface 40a, and a screw 44d (see FIG. 3) is inserted into the slit 44e to be coupled to the adapter 4. The slide lock 44 is coupled to the adapter 4 so as to be movable with respect to the adapter along the slit 44e. The slide lock 44 is provided for the purpose of further stabilizing a state of coupling between the adapter 4 and the arm 3. The slide lock 44 sandwiches parts of the adapter 4, the arm connection part 41, and the device coupling part 3*f* between the contact part 44*a* and the locking part 44*b* when the arm connection part 41 is fitted to the device coupling part 3*f* (see FIG. 8).

A hole 40*d* (see FIG. 4) penetrating the adapter 4 in a thickness direction is formed in the second flat surface 40*b* of the adapter 4. The medical device holding part 42 is inserted into the hole 40*d* of the second flat surface 40*b* of the adapter 4 and attached thereto.

The medical device holding part 42 is a screw-like member and has a head part 42*a* and a shaft 42*b* in which a screw thread 42*d* is formed as shown in FIG. 4. The medical device holding part 42 has an insertion hole 42*c* formed to penetrate therethrough in the entire length from the head part 42*a* to the shaft 42*b*.

A rotation-preventing member 7 is inserted into the insertion hole 42*c* of the medical device holding part 42. The rotation-preventing member 7 is a cylindrical member formed of an elastic member. A through hole 70 is formed in the rotation-preventing member 7 over the entire length in the longitudinal axis direction. The rotation-preventing member 7 is capable of being inserted into the insertion hole 42*c* and has an outer diameter that allows frictional engagement with an inner surface of the insertion hole 42*c*. A length of the rotation-preventing member 7 in the longitudinal axis direction is longer than a total length of the insertion hole 42*c*. An inner diameter of the through hole 70 of the rotation-preventing member 7 has a size in which the long part 301 of the medical device 300 is capable of being inserted into the through hole 70.

The balance correction member 5 is a heavy object in a nut shape as shown in FIGS. 2 and 4 and is attached to the adapter body 40. The balance correction member 5 has a through hole 50 formed at a center part of the balance correction member 5. A knob 53 is formed around an outer circumference of the balance correction member 5. The balance correction member 5 functions as a weight.

A screw groove 50*b* is formed in the through hole 50 in the region from an end part on a first surface 51 side facing the adapter 4 to a middle part in the longitudinal axis direction. The screw groove 50*b* is formed to be screwed to the screw thread 42*d* of the medical device holding part 42. The through hole 50 has a tapered part 50*a*. The tapered part 50*a* is formed such that an opening diameter thereof gradually decreases from the middle part (a terminal end of the screw groove 50*b*) toward an end part on a second surface 52 that is the opposite side of the first surface 51. An opening diameter of the through hole 50 on the second surface 52 side is smaller than an outer diameter of the rotation-preventing member 7.

A drape connection part 43 is further provided in the adapter 4 as shown in FIG. 2. The drape connection part 43 is provided between the arm connection part 41 and the device coupling part 3*f*. A drape 400 is attached to the drape connection part 43. The drape 400 divides the region on the arm side above the drape connection part 43 (unclean area) from the region on the adapter side above the drape connection part 43 (the medical device side; clean area). The drape 400 is provided to secure a clean area for the medical device 300.

Next, usage of the medical device holding apparatus 1 and the medical device 300 will be described.

The shaft 42*b* of the medical device holding part 42 is inserted into the hole 40*d* of the adapter body 40, and the head part 42*a* comes in contact with the second flat surface 40*b* of the adapter body 40 as shown in FIG. 4.

The rotation-preventing member 7 is inserted into the insertion hole 42*c* of the medical device holding part 42. The rotation-preventing member 7 is inserted in a state in which an end thereof is flush with an end surface of the head part 42*a* of the medical device holding part 42 and a part of the rotation-preventing member 7 protrudes outside from the end part of medical device holding part 42 on the shaft 42*b* side. The rotation-preventing member 7 inserted into the insertion hole 42*c* is frictionally engaged with the inner surface of the insertion hole 42*c*.

The balance correction member 5 is externally mounted on the shaft 42*b* of the medical device holding part 42. Specifically, the balance correction member 5 is brought close to the medical device holding part 42 as shown in FIG. 4. The shaft 42*b* of the medical device holding part 42 is inserted into the hole 40*d* of the adapter body 40. The shaft 42*b* is inserted into the through hole 50 of the balance correction member 5, the screw thread 42*d* is screwed to the screw groove 50*b*, and thereby the balance correction member 5 is engaged with the medical device holding part 42. At this time, the rotation-preventing member 7 protruding outside the medical device holding part 42 comes in contact with the tapered part 50*a*, is pressed in a radial direction, and thus is elastically deformed, which causes the through hole 70 to have a reduced diameter.

The adapter 4 in which the medical device holding part 42, the rotation-preventing member 7, and the balance correction member 5 are connected is attached to the arm 3. The shaft 41*a* of the arm connection part 41 is inserted and fitted into the drape connection part 43 and the device coupling part 3*f* as shown in FIG. 2. Then, the slide lock 44 is caused to slide to cause the locking part 44*b* to be locked to the device coupling part 3*f* and thereby the adapter 4 and the arm 3 are held in a coupled state.

The long part 301 of the medical device 300 is inserted into the adapter 4 that has been coupled to the arm 3. At this time, screwing of the balance correction member 5 to the medical device holding part 42 is loosened to cancel the reduced-diameter state of the protruding part of the rotation-preventing member 7 with respect to the medical device holding part 42. In this state, the long part 301 is inserted, and then when the balance correction member 5 is screwed onto the medical device holding part 42 again, the protruding part of the rotation-preventing member 7 is brought into a reduced-diameter state, and the long part 301 is held in frictional engagement with the rotation-preventing member 7. As a result, rotation of the long part 301 held by the medical device holding part 42 around the longitudinal axis is prevented by the rotation-preventing member 7.

A frictional engagement force between the long part 301 and the rotation-preventing member 7 is set such that the long part 301 is prevented from rotating in a state in which no external force is applied to the medical device 300, but when a user exerts a force on the medical device 300 to rotate the medical device around the longitudinal axis, the long part 301 is made to be relatively rotatable.

The balance correction member 5 is attached in order to cause the arm 3 to remain stationary in a balanced posture while attaching the medical device 300 to the arm 3 via the adapter 4.

"A balanced posture is taken" refers to a state in which the arm 3 itself remains stationary with respect to the base 8 at a desired position. That is, a position of the arm 3 remains stationary even when a user is not touching the arm 3 or the medical device 300. For example, the above-described state includes not only a state in which the arm 3 maintains a horizontally balanced posture but also a state in which the arm remains stationary at a position at which a height of a medical device attached to the arm from the floor is a desired height while tilting with respect to the horizontal flat surface, a state in which the arm 3 returns stationary in a previous posture even if the medical device 300 attached to the arm 3 is moved in accordance with a swing of the swing arm 3e, and the like.

The medical device holding apparatus 1 is configured such that the arm moving mechanism 200 enables the arm 3 to stand in a still posture in a state in which the medical device 300 is attached to the distal end part 3b of the arm 3. Medical devices have different weights and positions of the center of gravity at the time of attachment of the arm 3 according to their different types and sizes. If a plurality of devices of different types and sizes are used as medical devices 300, the arm 3 changes its posture according to the types of the medical devices 300 when the medical devices 300 are switched. In such a case of a conventional holding apparatus, a user performs the work of adjusting the counterweight and adjusting a balanced posture of the arm.

However, in the medical device holding apparatus 1, the balance correction member 5 functions as a weight for correction, and a change in weight balance between before and after replacement of the medical devices 300 is corrected according to an attachment position of the adapter 4. As a result, a state of a still posture of the arm 3 before and after replacement of the medical devices 300 is maintained. Weights and sizes of the balance correction member 5 are set individually for the plurality of medical devices 300, and a plurality of balance correction members 5 individually corresponding to each of the medical devices 300 are provided and attached to the adapter 4.

Specifically, an arbitrary reference device is selected from the medical devices 300. In a state in which the selected reference medical device 300 is attached to the medical device holding apparatus 1 via the adapter 4, the counterweights 20a and 20b are set so that the arm 3 maintains a balanced posture. In addition, the weight of the reference medical device 300 and the adapter 4 when the reference medical device 300 is attached to the adapter 4 is set as a reference weight.

The respective medical devices 300 and the balance correction member 5 are combined such that the combined weight of each corresponding pair of medical device 300 and balance correction member 5 together with the adapter 4 is equal to the reference weight. Specifically, a weight of each balance correction member 5 is set according to the difference between a combined weight of the adapter and corresponding medical devices 300 to be used and the reference weight. For example, when the combined weight of the medical device 300 and adapter 4 is lighter than the reference weight, the balance correction member 5 is set to have a weight that is equal to a difference in weight from the reference weight. In a case where the combined weight of the medical device 300 and adapter 4 is heavier than the reference weight, the balance correction member 5 is set such that a balanced posture equivalent to that when a medical device having the reference weight is mounted is taken by adjusting the center of gravity of the balance correction member 5 by changing a size and a shape thereof. Alternatively, a balance correction member 5 of which a center of gravity has been adjusted by changing a position at which the balance correction member is attached to the adapter 4 may be provided. For example, the balance correction member 5 may be attached between a part of the medical device 300 on the base end side and the second flat surface 40b of the adapter body 40. That is, a weight or the center of gravity of the medical device 300 while the medical device is attached to the adapter 4 is adjusted by using the balance correction member 5, and therefore total weights of each set of the adapter 4 with corresponding pair of balance correction member 5 and medical device 300 is equivalent to a weight in the state in which the reference medical device 300 is attached to the adapter 4 (even if the medical devices 300 have different weights) by attaching each medical device 300 to the adapter 4 together with an optimum balance correction member 5. As a result, a balanced posture of the arm 3 is capable of being controlled similarly to the case in which the reference medical device 300 is attached. Therefore, irrespective of which of a plurality of medical devices 300 having different weights and centers of gravity is attached to the arm 3, a weight balance of the arm 3 is maintained, and thus adjustment of the counterweight is unnecessary.

The medical device holding apparatus 1 is configured such that, if a combined weight for each corresponding set of adapter 4, balance correction member 5, and medical device 300 is within the range of 15% from the reference weight, the weight balance of the arm 3 does not change even if the medical device 300 is replaced and the arm 3 remains stationary as when a reference medical device 300 is attached. The medical device holding apparatus 1 can stably hold the medical device 300 while guaranteeing a certain level of operability as long as a rate of change in a combined weight of the adapter 4 having the balance correction member 5 and corresponding medical device 300 attached thereto from the reference weight is within 15%, the difference in weight having been corrected by the balance correction member 5. Although the operation feeling of the arm 3 then becomes very heavy, a balance is capable of being maintained in a medical device 300 in which the rate of change exceeds 15%.

As a result of the medical device holding apparatus 1 having the above-described configuration, when a user replaces the adapter 4 in order to replace the medical device 300, the arm 3 is capable of maintaining a weight balance and remains stationary in a balanced posture similarly to before the replacement of the medical device 300. Therefore, the work of adjusting a counterweight as in conventional holding apparatuses is unnecessary. In addition, since the counterweights 20a and 20b are disposed in the unclean area, the counterweight adjustment work becomes unnecessary, and as a result, the user does not need to perform operations in the unclean area during surgery.

As described above, the balance correction member 5 is connected to the medical device holding part 42 and the rotation-preventing member 7. A plurality of rotation-preventing members 7 may also be provided according to an outer diameter of the long part 301 of each medical device 300. Thus, a combination of the balance correction member 5, and the medical device holding part 42 and the rotation-preventing member 7 may be set according to each medical device 300, and a plurality of adapters 4 to which these elements are attached may be provided.

At a time of using the medical system 100, a plurality of adapters 4 are individually provided according to each medical device 300. A user uses the medical device 300 by attaching the adapter 4 corresponding to the medical device 300 to be used to the arm 3.

Here, in order to achieve efficient working during use and a shorter working time, it is preferable that a correspondence between the plurality of adapters 4, the balance correction members 5, and each medical device 300 be easily ascertained. For a similar purpose, in a case where there are a plurality of medical device holding parts 42 and anti-rotation members 7 having similar appearances, it is desirable to prevent incorrect combinations in which parts that are different from the desired medical device holding part 42 and rotation-preventing member 7 are erroneously attached to the adapter body 40. Therefore, it is more preferable for the adapter 4 to have configurations as shown in the following modified examples.

Figure 5:
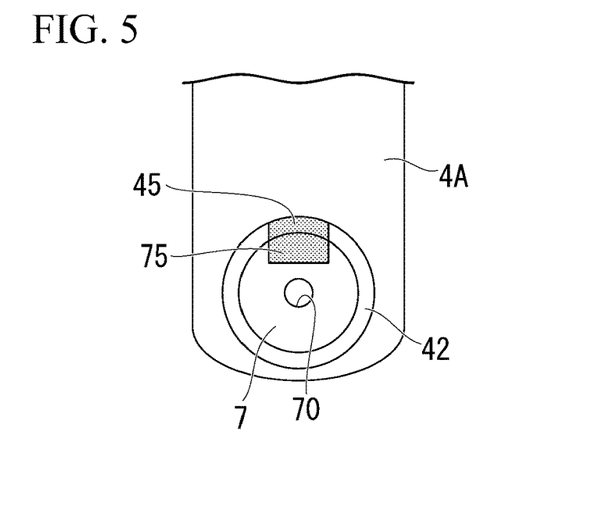
FIG. 5 is a front view showing a modified example of the medical device holding apparatus shown in FIG. 1.

An adapter 4A of a modified example of the adapter 4 shown in FIG. 1 is shown in FIG. 5. In the following description, portions having the same configurations as those in the medical device holding apparatus 1 and the medical system 100 described above are denoted by the same reference numerals, and a detailed description thereof is omitted. As shown in FIG. 5, markers 45 and 75 are provided at the medical device holding part 42 and the rotation-preventing member 7 respectively.

The markers 45 and 75 in the same color are attached to the medical device holding part 42 and the rotation-preventing member 7 corresponding to the balance correction member 5 set according to each medical device 300. As a result, when a user attaches the medical device holding part 42 and the rotation-preventing member 7 to the adapter body 40, a combination of the necessary medical device holding part 42 and rotation-preventing member 7 can be easily recognized and an incorrect combination can be prevented.

The balance correction member 5 is used by selecting a suitable member according to a weight and a position of the center of gravity of the medical device 300. Since the balance correction member 5 functions as a weight, the balance correction member 5 has different sizes and shapes according to types of medical device 300. If the balance correction member 5 has different shapes and sizes, the medical device holding part 42 that is screwed thereto also has different shapes. Furthermore, the medical device holding part 42 may be removed from the adapter 4 at the time of cleaning. Although not shown, if a marker in the same color as those of the medical device holding part 42 and the rotation-preventing member 7 is attached to the balance correction member 5, a combination of the medical device holding part 42, the rotation-preventing member 7, and the balance correction member 5 for the adapter 4 can be easily recognized and an incorrect combination can be prevented.

Figure 6:
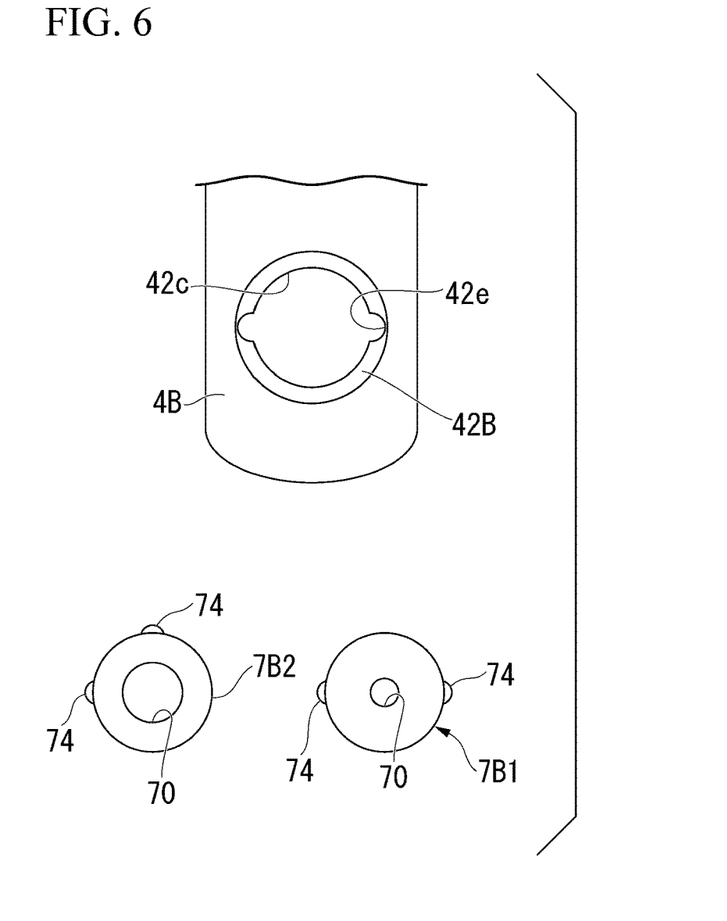
FIG. 6 is a front view showing a modified example of part of the medical device holding apparatus shown in FIG. 1.
Figure 7:
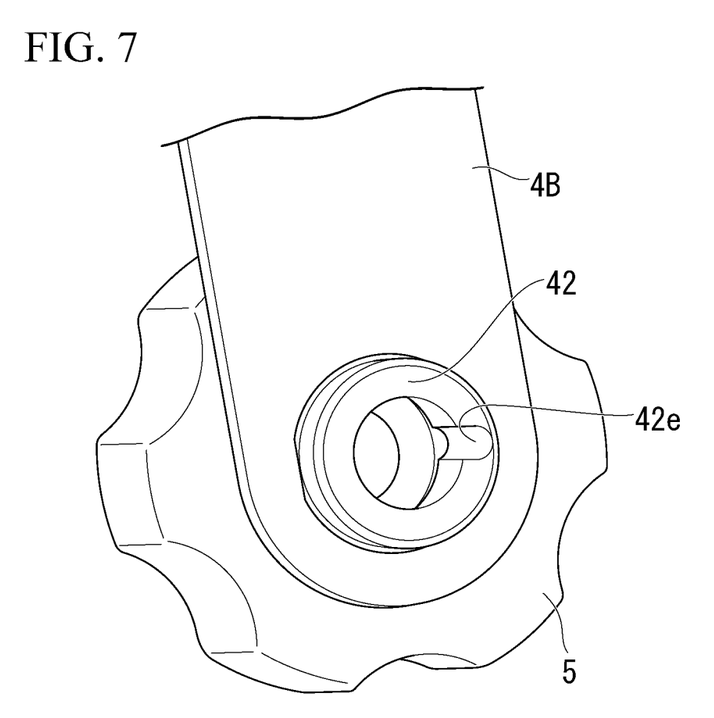
FIG. 7 is a perspective view of the modified example shown in FIG. 6.

An adapter 4B of a modified example of the adaptor 4 shown in FIG. 1 is shown in FIGS. 6 and 7. FIG. 6 shows a diagram in which the adapter 4B with a medical device holding part 42B attached thereto and two rotation-preventing members 7B1 and 7B2 are viewed in the longitudinal axis direction. An outer diameter of the long part 301 of the medical device 300 may differ depending on the type of the device. Thus, in order to stably hold each of medical devices 300 with the long parts 301 having different outer diameters respectively, a plurality of rotation-preventing members 7B 1 and 7B2 with through holes 70 having different inner diameters are necessary.

In this modified example, a groove 42e is formed in the insertion hole 42c of the medical device holding part 42B over the entire length in the penetration direction as shown in FIG. 7. A convex part 74 protruding in the radial direction is formed on each outer circumferential surface of the rotation-preventing members 7B 1 and 7B2.

The groove 42e may be formed such that the number of grooves of the insertion hole 42c, a position thereof in the insertion hole 42c in a circumferential direction, and a size and a shape thereof differ according to a type of the medical device 300 to be held. Likewise, the number of convex parts 74 of the rotation-preventing member 7B 1, 7B2, a position of the rotation-preventing member 7B1, 7B2 in the circumferential direction, and the size and a shape thereof may differ according to a type of the medical device 300 to be held.

If there are a plurality of types of medical device holding part and rotation-preventing member, an incorrect combination in which the elements are attached in a wrong correspondence may occur. In order to prevent such an incorrect combination, the convex part 74 of the rotation-preventing member 7B1, 7B2 and the groove 42e of the medical device holding part 42B are each formed at positions specific to the corresponding members.

The rotation-preventing member 7B 1, 7B2 is inserted into the insertion hole 42c of the medical device holding part 42B. At this moment, the convex part 74 formed on the rotation-preventing member 7B 1, 7B2 is inserted into the groove 42e formed in the insertion hole 42c so that the convex part is engaged and aligned therewith, and thereby the rotation-preventing member 7B1, 7B2 is inserted into the insertion hole 42c. As a result, only a predetermined rotation-preventing member corresponding to the insertion hole 42c of the medical device holding part 42B can be inserted thereinto (e.g., the rotation-preventing member 7B 1 on the right side in the example shown in FIG. 6), a rotation-preventing member having a different configuration and convex part (e.g., the rotation-preventing member 7B2 on the left side in the example shown in FIG. 6) is not inserted into the insertion hole 42c, and thus an incorrect combination can be prevented.

The rotation-preventing members 7B1 and 7B2 are held without rotating with respect to the medical device holding part 42B by engaging the rotation-preventing members 7B 1 and 7B2 and the medical device holding part 42B with each other due to the convex part 74 and the groove 42e. Therefore, the rotation-preventing members 7B can be prevented from rotating with respect to the medical device holding part 42B, and also the long part 301 can be prevented from rotating, more reliably when an operation of rotating the medical device 300 around the longitudinal axis of the long part 301 is performed.

The inside of the insertion hole 42c of the adapter 4B may be cleaned. The groove 42e is formed in the insertion hole 42c of the medical device holding part 42B over the entire length of the insertion hole as shown in FIG. 7. Thus, a cleaning brush is capable of being inserted into the insertion hole 42c through the entire length at the time of cleaning the adapter 4B, and thus even corners of the adapter 4B is capable of being easily cleaned.

According to the above-described medical device holding apparatus 1 and the medical system 100, complexity of the operation for replacing the medical devices 300 can be reduced, work efficiency can be enhanced, and a surgical operation time can be shortened. In addition, efficiency in the work of replacing a plurality of medical devices 300 and adapters 4 can be increased and an incorrect combination can be prevented.

Figure 8:
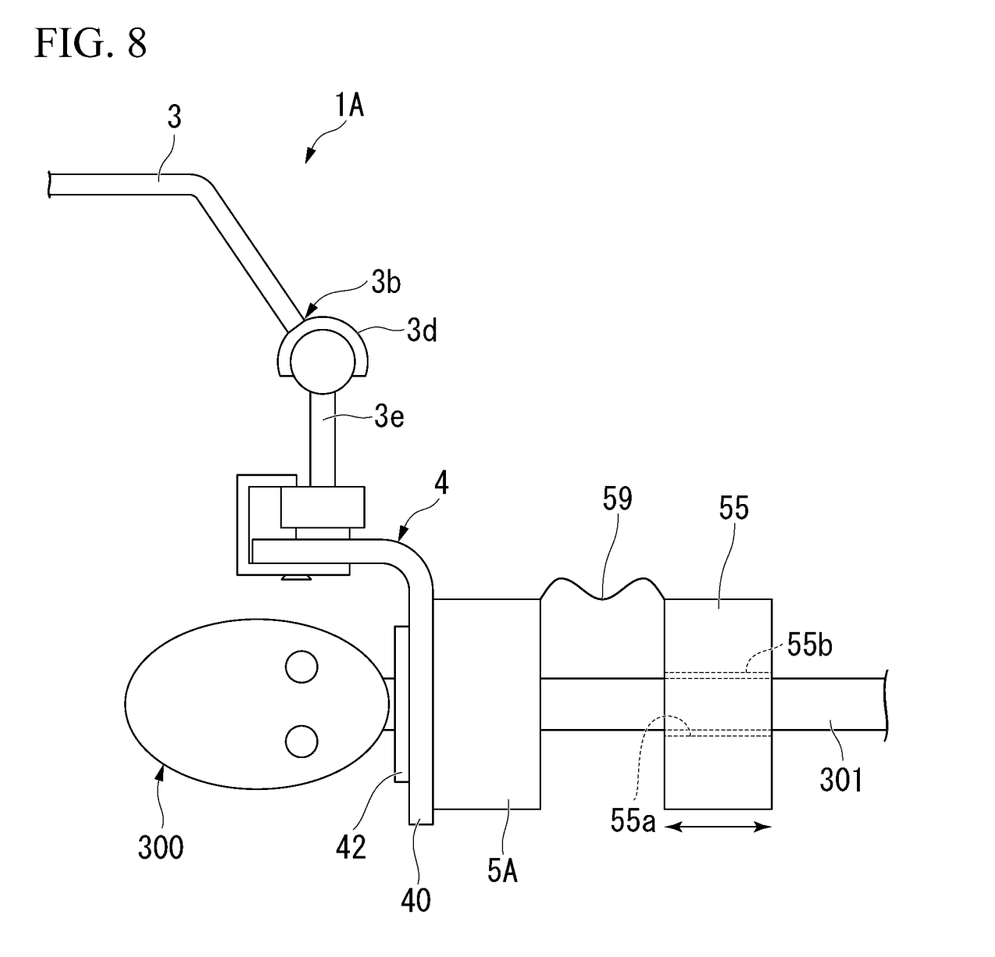
FIG. 8 is a side view showing an adapter and a balance correction member of a medical device holding apparatus of the disclosed embodiments.

A medical device holding apparatus 1A according to an exemplary embodiment will be described. FIG. 8 is a view showing surroundings of an adapter 4 of the medical device holding apparatus 1A. The medical device holding apparatus 1A has a balance correction member with a configuration different from the medical device holding apparatus 1, as shown in FIG. 8.

The medical device holding apparatus 1A has a balance correction member 5A for holding a medical device 300 attached to a swing arm 3e in a predetermined posture.

The balance correction member 5A is configured such that an auxiliary balance correction member 55 is connected via a wire 59 to a balance correction member 5 that is similar to that of medical device holding apparatus 1. The wire 59 causes the auxiliary balance correction member 55 not to be separated from the balance correction member 5. The auxiliary balance correction member 55 is a weight member formed of a disk-like member having an insertion hole 55a.

A tube 55b formed of an elastic member is inserted into and fixed to the insertion hole 55a. A long part 301 of a medical device 300 is inserted into the insertion hole 55a. The auxiliary balance correction member 55 is slidable against the long part 301.

Since the long part 301 comes in contact with the inner circumferential surface of the tube 55b, when the auxiliary balance correction member 55 is caused to slide against the long part 301, sliding resistance is generated due to a frictional force caused between the tube 55b and the long part. A frictional force between the long part 301 and the tube 55b is set such that a user can grab and slide the auxiliary balance correction member 55, and when no external force is applied, the auxiliary balance correction member 55 does not slide. In addition, the frictional force between the long part 301 and the tube 55b is set at a level that the auxiliary balance correction member does not slide under its own weight even if the long part 301 is inclined is generated between the long part 301 and the tube 55b in a case where no external force is applied directly to the auxiliary balance correction member 55.

There are cases in which the swing arm 3e swings due to a position of the center of gravity of the medical device 300 and thus the medical device 300 is inclined with respect to a horizontal flat surface and has an unstable posture. In such a case, by sliding the auxiliary balance correction member 55 of the balance correction member 5A against the long part 301, the position of the center of gravity of the medical device 300 attached to the adapter 4 can be corrected to an appropriate position. As a result, even if the swing arm 3e swings, the medical device 300 can be maintained in a desired equilibrium state.

Figure 9:
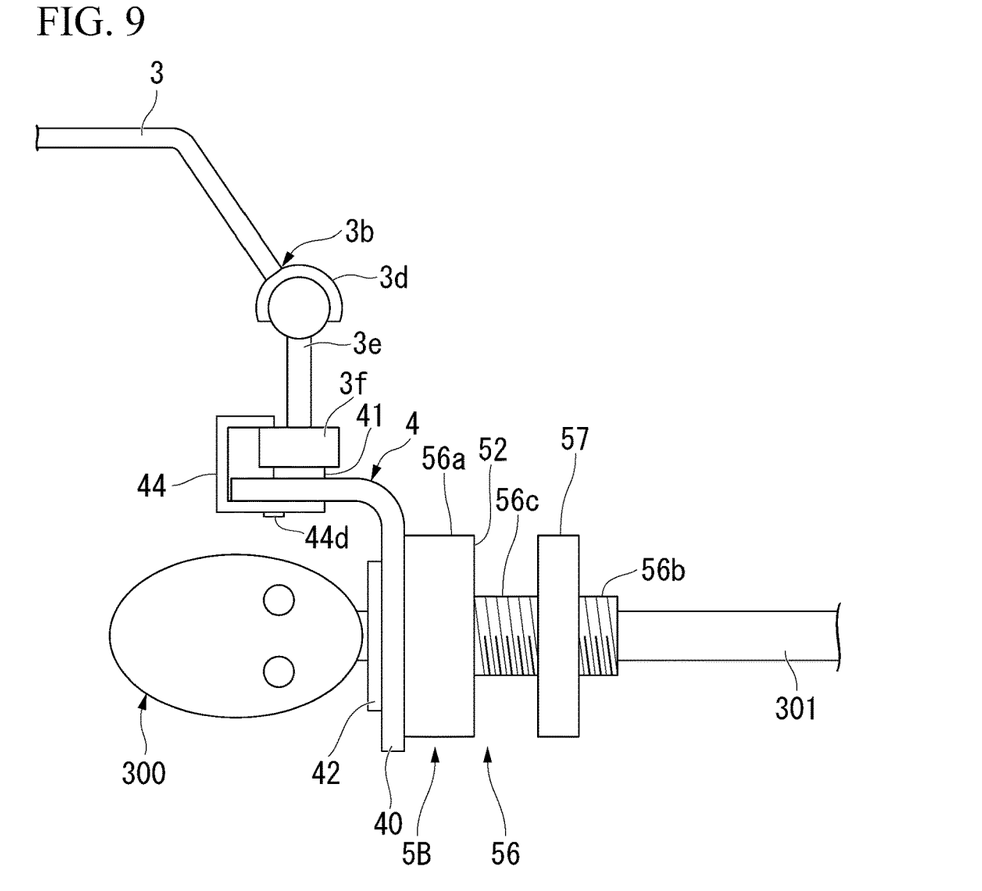
FIG. 9 is a side view showing a modified example of the balance correction member shown in FIG. 8.

A configuration of the balance correction member 5A is not limited to the configuration shown in FIG. 8. FIG. 9 shows a modified example of the balance correction member 5A. A balance correction member 5B shown in FIG. 9 includes a first member 56 and a second member 57. The first member 56 has a head part 56a with the same configuration as that of the balance correction member 5 of the medical device holding apparatus 1and includes a tubular shaft part 56b protruding from a second surface 52 of the head part 56a in a longitudinal axis direction. The tubular shaft part 56b is cylindrical and has an insertion hole (not shown) formed to extend from an insertion hole 43c of the head part 56a. A screw thread 56c is formed on an outer circumferential surface of the tubular shaft part 56b.

The second member 57 is a ring-like heavy object and has a screw groove (not shown) that can be screwed to the screw thread 56c of the first member 56, the screw groove being formed on an inner circumferential surface. The second member 57 is movable with respect to the tubular shaft part 56b in the longitudinal axis direction. A long part 301 of a medical device 300 is inserted into an insertion hole 43c of the first member 56. By moving the second member 57 with respect to the tubular shaft part 56b with the medical device 300 attached to an adapter 4, the position of the center of gravity of the medical device 300 attached to the adapter 4 can be corrected to an appropriate position. As a result, even if the swing arm 3e swings, the medical device 300 can be maintained in a desired equilibrium state.

The balance correction members 5A and 5B can be used not only for correction when the swing arm 3e swings but also can be used as the balance correction member for the arm 3 of the medical device holding apparatus 1. If the balance correction members 5A and 5B are used, a user can perform fine adjustment for balance on the center of gravity.

Although embodiments of the present invention have been described above, a technical scope of the present invention is not limited thereto, and a combination of constituent elements can be changed in a scope not departing from the gist of the present invention, or each constituent element can be subject to various modifications or can be eliminated.

Although the example in which the medical device holding part 42 is provided as a separate body from the adapter body 40 has been introduced in the above-described embodiments, a configuration of the medical device holding part 42 is not limited thereto, and the medical device holding part can be formed to be integrated with the adapter body 40. Although the example in which the medical device holding part 42 is screwed to the balance correction member 5 has been introduced in the above-described embodiments, an engagement means of the medical device holding part 42 with the balance correction member 5 is not limited thereto, and both the elements can be engaged with each other by providing an engagement means in each of the members.

Figure 10:
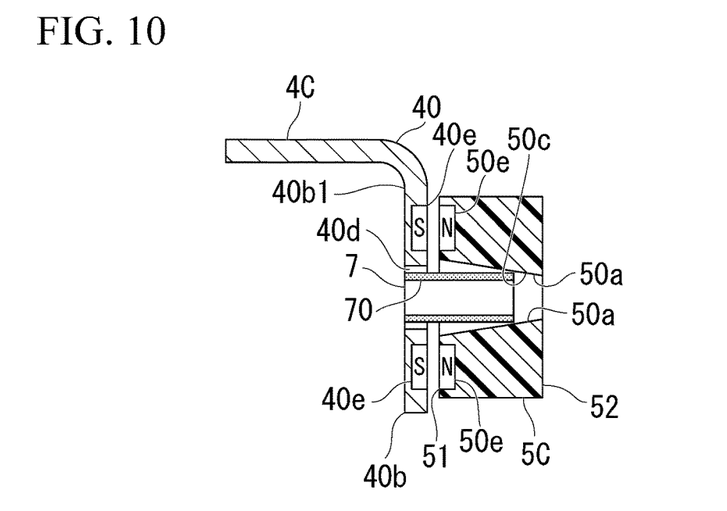
FIG. 10 is a perspective view showing a modified example of part of the medical device holding apparatus shown in FIG. 1.

For example, FIG. 10 shows a schematic cross-sectional view of an adapter 4C of a modified example of the adaptor 4 shown in FIG. 1. The adapter 4C has a different configuration from that of the medical device holding part 42 of the adaptor 4, as shown in FIG. 10.

A magnetic pole 40e is provided in a second flat surface 40b of an adapter body 40. The magnetic pole 40e is provided around a hole 40d of the adapter body 40 in ring shape. A balance correction member 5C is a circular columnar member and a through hole 50c is formed along a central line of the circle. The through hole 50c has a tapered part 50a formed such that an opening diameter thereof gradually decreases from the end part on a first surface 51 side coming in contact with the second flat surface 40b of the adapter body 40 toward the end part on a second surface 52 side that is the opposite side of the first surface 51. An opening diameter of the through hole 50c on the second surface 52 side is smaller than an outer diameter of a rotation-preventing member 7.

An annular magnetic pole 50e is provided around the opening of the through hole 50c on the first surface 51. The magnetic pole 50e of the balance correction member 5C is provided at a position at which the magnetic pole 50e faces the magnetic pole 40e of the adapter body 40 when being brought in contact with the second flat surface 40b of the adapter body 40. The magnetic pole 50e of the balance correction member 5C is an N pole, and the magnetic pole 40e of the adapter body 40 is an S pole.

The rotation-preventing member 7 is inserted into a hole 40d of the adapter body 40. One end of the rotation-preventing member 7 is disposed to be flush with a surface 40b1 on one side of the second flat surface 40b of the adapter body 40, and the other end of the rotation-preventing member 7 is inserted into the hole to protrude from the second flat surface 40b. The rotation-preventing member 7 is frictionally engaged with the inner surface of the hole 40d. That is, in the present modified example, the second flat surface 40b functions as a medical device holding unit.

When the first surface 51 of the balance correction member 5C is brought close to the second flat surface 40b of the adapter body 40 so that the protruding part of the rotation-preventing member 7 is inserted into the through hole 50c of the balance correction member 5C, the adapter body 40 and the balance correction member 5C are attracted and brought in contact with each other due to a magnetic force of the magnetic poles 40e and 50e, and this contact state is maintained. At this moment, the rotation-preventing member 7 protruding from the second flat surface 40b of the adapter body 40 comes in contact with the tapered part 50a, is pressed in a radial direction, and thus is elastically deformed, which causes a through hole 70 to have a reduced diameter.

According to the present modified example, complexity of the operation for replacing the medical devices 300 can be reduced, work efficiency can be enhanced, and a surgical operation time can be shortened. In addition, since the adapter body 40 is caused to join to the balance correction member 5C due to a magnetic force, work of attaching the balance correction member 5C to the adapter body 40 becomes easier.

Further, a configuration of magnetic poles provided in the adapter body 40 and the balance correction member 5C is not limited to the above-described configuration as long as a state in which the balance correction member 5C joins to the adapter body 40 can be maintained.

Although the example in which the arm 3 is caused to remain stationary by attaching a counterweight to an arm moving mechanism to maintain a balanced posture of the arm has been described above, a counterweight is not an essential configuration, and any element can be used as long as it can allow the arm to remain stationary in a predetermined balanced posture.

Figure 11:
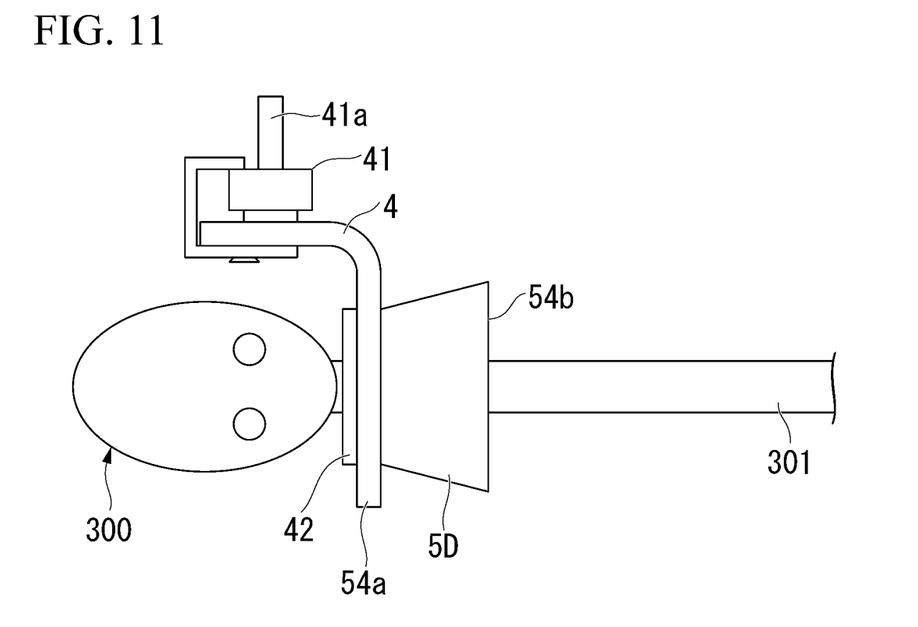
FIG. 11 is a side view showing a modified example of part of the medical device holding apparatus shown in FIG. 1.

Next, an example in which the center of gravity is adjusted by changing a size and a shape of a balance correction member 5 is shown in FIG. 11. In the modified example shown in FIG. 11, a balance correction member 5D has as truncated conical shape. The balance correction member 5D is disposed such that a surface 54a having a small bottom area of the truncated conical shape comes in contact with a second flat surface 40b of an adapter 4, and a surface 54b having a large bottom area thereof is positioned on a tip end side of the medical device 300. In this case, since the center of gravity of the balance correction member 5D is positioned in an area on the surface 54b side having the large bottom area, a position of the center of gravity of any balance correction member having the same weight can be changed.

According to the present modified example, the complexity of the operation for replacing the medical devices 300 can be reduced, work efficiency can be enhanced, and a surgical operation time can be shortened. In addition, the modified example is preferable for a case where a position of the center of gravity of a medical device 300 needs to be adjusted.

Although the example in which the drape connection part and the drape are provided has been described above, the drape connection part and the drape are not essential configurations for the purpose of causing the arm to remain stationary while maintaining a balanced posture even if a medical device is replaced.

A coupling structure of the device coupling part and an arm connection part is not limited to that of the above-described embodiments, and a configuration in which another intermediate member or the like is provided may be applied.

EXAMPLE

Balance states of the arm 3 of the medical device holding apparatus 1 were tested by using the medical device holding apparatus 1 and the medical system 100 described above with respect to FIG. 1, preparing a plurality of types of medical devices A to L, and appropriately attaching balance correction members i to iii having different weights. Table I shows combinations of medical devices and the balance correction members and a rate (unit: %) of change in weight in a case where correction was performed using the balance correction members from a predetermined weight.

TABLE 1

| Type of Medical Device | Type of Balance Correction Member | Rate of Change in Weight in Case where Correction was performed using Balance Correction Members from Reference Weight (Unit: %) |
|---|---|---|
| A | i | 11 |
| B | ii | 9 |
| C | ii | −10 |
| D | i | 5 |
| E | i | −6 |
| F | ii | −10 |
| G | ii | 9 |
| H | i | 5 |
| I | None | 0 |
| J | iii | −2 |
| K | i | −5 |
| L | ii | −10 |

The medical device I did not need to have a balance correction member attached thereto since the medical device had a substantially equal weight to that of a reference medical device and a weight balance of the arm was attained without a balance correction member.

A weight of an adapter and a reference medical device when the reference medical device has been attached to the adapter without a balance correction member is assumed to be a reference weight. A rate of change in weight in a case where correction was performed using a balance correction member from the reference weight was obtained by dividing, by the reference weight, a weight of an adapter and a medical device with balance correction member in a case where each of the medical devices A to L was attached to each adapter with one of the balance correction members i to iii attached thereto in a combination corresponding to each of the medical devices A to L. The balance correction members i to iii were attached so that the rates of change of all the medical devices A to L came within the range from −15% to +15%. As a result that the medical devices A to L were sequentially replaced and attached to the medical device holding apparatus 1, the arm could maintain a weight balance.

What is claimed is:
1. A medical system comprising:
a first medical device;
a second medical device having a different weight than the first medical device;
a base having a counterweight;
an arm having a first end coupled to the counterweight;
a connector assembly that is detachably attachable to a second end of the arm, the first medical device, and the second medical device, and is configured to connect the second end of the arm to any one of the first medical device and the second medical device;

a first weight that is detachably attachable to the connector assembly and is configured to attain a weight balance between the first end of the arm and the second end of the arm when the first medical device is attached to the connector assembly; and
a second weight that is detachably attachable to the connector assembly and is configured to attain a weight balance between the first end of the arm and the second end of the arm when the second medical device is attached to the connector assembly.

2. The medical system according to claim 1, wherein a combined weight M1 of the connector assembly, the first medical device, and the first weight and a combined weight M2 of the connector assembly, the second medical device, and the second weight satisfy the following relationship:

$$1.15 \geq M2/M1 \geq 0.85.$$

3. The medical system according to claim 1, further comprising a U-shaped lock that is slidably engaged with the connector assembly and configured to stabilize the connector assembly and the arm when the connector assembly and the arm are in an attached state.

4. The medical system according to claim 1, wherein the connector assembly comprises an elastic cylinder member having a through hole configured to receive a portion of the first medical device or a portion of the second medical device in a state of frictional engagement.

5. The medical system according to claim 1, wherein the connector assembly is configured to directly connect the second end of the arm to any one of the first medical device and the second medical device.

6. The medical system according to claim 1, wherein the first medical device and the second medical device are interchangeably attachable to the connector assembly.

7. A medical device holding apparatus comprising:
a base having a counterweight;
an arm having a first end coupled to the counterweight;
a connector assembly that is detachably attachable to a second end of the arm and is configured to connect the second end of the arm to any one of a plurality of medical devices;
a plurality of weights that are each detachably attachable to the connector assembly and configured to attain a weight balance between the first end of the arm and the second end of the arm when a corresponding one of the plurality of medical devices is attached to the arm via the connector assembly,
wherein the plurality of weights are interchangeable according to a type of the medical device to be attached to the arm.

8. The medical device holding apparatus according to claim 7, wherein the plurality of weights are interchangeable according to a weight of the medical device to be attached to the arm.

9. The medical device holding apparatus according to claim 7, wherein the plurality of weights are interchangeable according to a position of a center of gravity of the medical device when the medical device is attached to the arm.

10. The medical device holding apparatus according to claim 7, wherein a center of gravity of at least one of the plurality of weights is adjustable by detachably attaching the weight at different positions of the connector assembly.

11. The medical device holding apparatus according to claim 7, further comprising:
a drape configured to be attached between the arm and the connector assembly.

12. A medical device holding apparatus comprising:
a base having a counterweight;
an arm that is movable with respect to the base and has a first end coupled to the counterweight;
a connector assembly that is detachably attachable to a second end of the arm, a first medical device, and a second medical device, and is configured to connect the second end of the arm to any one of the first medical device and the second medical device;
a first weight that is detachably attachable to the connector assembly and is configured to adjust a weight balance between the first end of the arm and the second end of the arm so that the arm is held at a desired position when the first medical device is attached to the arm via the connector assembly; and
a second weight that is detachably attachable to the connector assembly and is configured to adjust a weight balance between the first end of the arm and the second end of the arm so that the arm is held at a desired position when the second medical device is attached to the Mil via the connector assembly.

* * * * *